United States Patent [19]
Itoh et al.

[11] Patent Number: 5,523,128
[45] Date of Patent: Jun. 4, 1996

[54] LIQUID CRYSTAL DISPLAY DEVICE

[75] Inventors: Nobuyuki Itoh, Nara; Masami Kido, Tenri; Shizuo Murata; Yukino Abe, both of Ichihara, all of Japan

[73] Assignees: Sharp Kabushiki Kaisha; Chisso Corporation, both of Osaka, Japan

[21] Appl. No.: 314,351

[22] Filed: Sep. 28, 1994

[30] Foreign Application Priority Data

Sep. 28, 1993 [JP] Japan .................................. 5-241327

[51] Int. Cl.⁶ .............................................. G02F 1/1337
[52] U.S. Cl. .................................. 428/1; 359/75; 359/78
[58] Field of Search ............................. 428/1; 359/75–79

[56] References Cited

FOREIGN PATENT DOCUMENTS

| 0282254 | 9/1988 | European Pat. Off. . |
|---|---|---|
| 0415447A1 | 3/1991 | European Pat. Off. . |
| 0540829A1 | 5/1993 | European Pat. Off. . |
| 56-107216 | 8/1981 | Japan . |
| 62-56933 | 8/1987 | Japan . |
| 62-280824 | 12/1987 | Japan . |
| 64-24234 | 1/1989 | Japan . |
| 64-59389 | 1/1989 | Japan . |

OTHER PUBLICATIONS

Koden, et al., "High Contrast C1–Uniform State of Surface Stabilized Ferroelectric Liquid Crystal Displays with High Pretilt Aligning Film," *Japan Display*, Dec. 1992, pp. 579–582.

Tagawa, et al., "Four States of Surface Stabilized Ferroelectric Liquid Crystal with Parallel Rubbing," *Japan Display*, Dec. 1992, pp. 519–522.

Koden, et al., "The States of Surface–Stabilized Ferroelectric Liquid Crystal with High–Pretilt Aligning Film," *Japanese Journal of Applied Physics*, vol. 30, No. 10B, Oct. 1991, pp. L1823–L1825.

Kanbe, et al., "High Resolution, Large Area FLC Display with High Graphic Performance," *Ferroelectrics*, Dec. 1991, vol. 114, pp. 3–26.

Surgay, et al., "The Joers/Alvey Ferroelectric Multiplexing Scheme," *Ferroelectrics*, Dec. 1991, vol. 122, pp. 63–79.

Rieker, et al., "Chevron Local Layer Structure in Surface-Stabilized Ferroelectric Smectic–C Cells," Dec. 1987, vol. 59, No. 23, pp. 2658–2661.

Ouchi, et al., "Switching Process in Ferroelectric Liquid Crystals; Disclination Dynamics of the Surface Stabilized States," *Japanese Journal of Applied Physics*, Jan. 1987, vol. 26, No. 1, pp. 1–14.

Numao, et al., "Design of Driving Waveform for Ferroelectric LCS," Sep. 1991, pp. 45–48.

Clark, et al., "Submicrosecond bistable electro–optic switching in liquid crystals," Jun. 1980, *Appl. Phys. Lett.*, 1980, vol. 36, No. 11, pp. 899–901.

Kondo, et al., "Surface–Induced Helix–Unwinding Process in Thin Homogeneous Ferroelectric Smectic Cells of DOBAMBC," *Japanese Journal of Applied Physics*, May 1983, vol. 22, No. 5, pp. L294–L296.

Patent Abstracts of Japan, vol. 015, No. 418 (p–1266) 23 Oct. 1991 and JP–A–03 171 933 (Mitsui Toatsu Chem Inc.) 24 Jul. 1991.

Patent Abstracts of Japan, vol. 015, NO. 410 (P–1264) 18 Oct. 1991 and JP–A–03 166 517 (Mitsui Toatsu Chem Inc.) 18 Jul. 1991.

Patent Abstracts of Japan, vol. 006, No. 233 (P–156) 19 Nov. 1982 and JP–A–57 133 432 (Canon KK) 18 Aug. 1982.

*Primary Examiner*—Alexander S. Thomas
*Attorney, Agent, or Firm*—David G. Conlin; Brian Michaelis

[57] ABSTRACT

A liquid crystal display device comprises a pair of substrates, a transparent electrode formed on each of the substrates, an orientation film covering the transparent electrode and a liquid crystal sealedly sandwiched between the pair of substrates, wherein the orientation film comprises a polyimide which is formed by a condensation polymerization of 2,2-bis[4-(4-aminophenoxy)phenyl]propane as an amine component and 1,2,4,5-benzenetetracarboxylic dianhydride as an carboxylic acid component, and is subjected to a uniaxial orientation treatment, and the liquid crystal has a smectic layer structure with its bending direction which is aligned with the direction of the uniaxial orientation treatment.

4 Claims, 6 Drawing Sheets

LIQUID CRYSTAL DISPLAY DEVICE

BACKGROUND OF THE INVENTION

1. Field of the Invention

The present invention relates to a liquid crystal display device, more particularly, to a liquid crystal display device using a ferroelectric liquid crystal.

2. Description of the Related Art

Conventional liquid crystal display devices mainly use nematic liquid crystals. The nematic liquid crystal display devices include Twisted Nematic (TN) type and Supertwisted Birefringence Effect (SBE) type. The TN-type liquid crystal display device has a disadvantage that satisfactory contrast cannot be obtained because the driving margin has been reduced in accordance with the development of the driving mode to be multiplex. Likewise, the SBE-type liquid crystal display device, or an improvement of the TN-type liquid crystal display which makes use of a larger twist angle, has a disadvantage of reduced contrast and slow response when applied to a large-scale display. To overcome the foregoing shortcomings, N. A. Clark and S. T. Lagerwall proposed a liquid crystal display device using a chiral smectic C liquid crystal, i.e., a ferroelectric liquid crystal in 1980, as disclosed in U.S. Pat. No. 4,367,924 and Japanese Unexamined Patent Publication 56-107216 (1981).

Figure 2A:
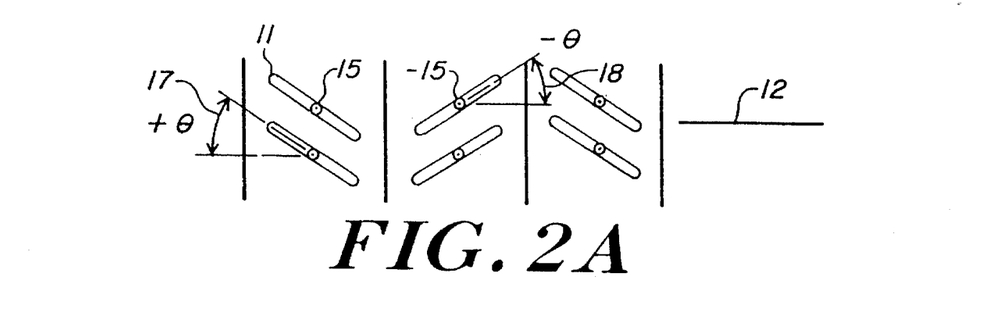
FIG. 2(a) to FIG. 2(d) are schematic representations illustrating the operational principle of a ferroelectric liquid crystal according to the present invention.
Figure 2B:
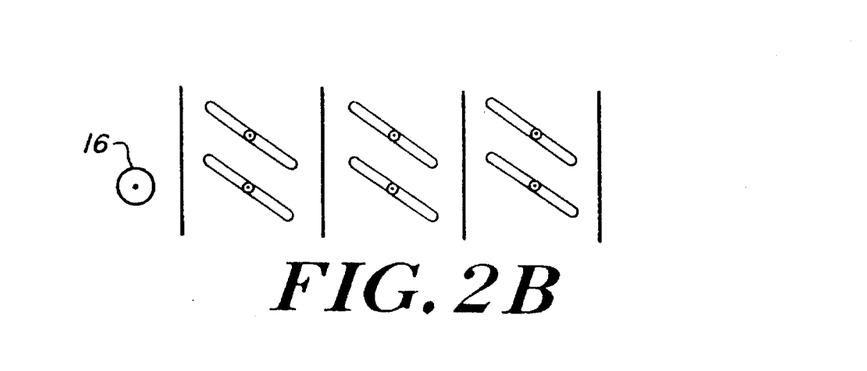
Figure 2C:
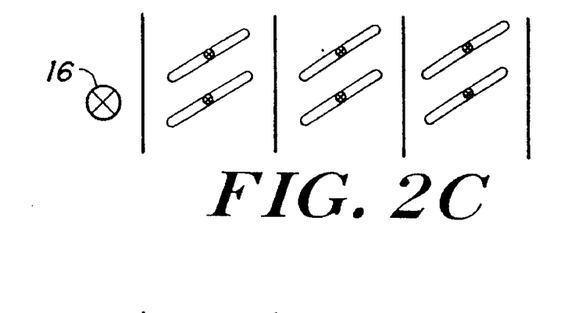
Figure 2D:
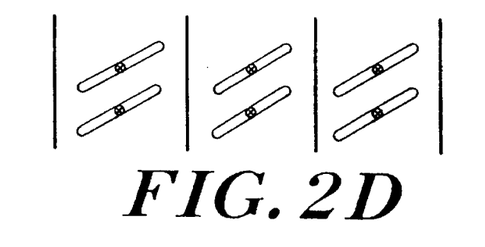

Unlike conventional nematic liquid crystal display devices utilizing electrical tilt effect developed by the dielectric anisotropy of liquid crystal molecules, the proposed liquid crystal display device utilizes rotatory power for aligning the polarity of spontaneous polarization of a ferroelectric liquid crystal with the polarity of electric field. This liquid crystal display device is mainly characterized by bistability, memory function, fast response, and wide viewing angle. When the ferroelectric liquid crystal is injected into a cell having a thin gap, the helical structure of the ferroelectric liquid crystal is unwound by the effect of the substrate boundary, and the bistability appears wherein there exist two stable regions in which liquid crystal molecules 11 are tilted by +θ degrees 17 and by −θ degrees 18 with respect to the normal of a smectic layer 12, as shown in FIG. 2(a). The application of electric field 16 to the ferroelectric liquid crystal in the cell allows the liquid crystal molecules 11 and their spontaneous polarization 15 to have a uniform orientation. Accordingly, the orientation of the liquid crystal molecules 11 can be switched from one state to the other by switching the polarity of the electric field to be applied.

The switching operation alters the birefringence of the ferroelectric liquid crystal in the cell and, hence, the light transmission can be controlled by interposing the cell between a pair of polarizers. In addition, even after the application of the electric field ceases, the liquid crystal molecules 11 retain the previous orientation, affected by the orientation restricting force of the substrate boundary, thereby exhibiting a memory effect. Furthermore, the direct interaction between the spontaneous polarization of the liquid crystal and the electric field provides a fast response display capability, wherein the time required for switching in the ferroelectric liquid crystal device is less than one thousandth of that required for switching in a nematic liquid crystal display device.

Researches are now being actively conducted concerning the applications of the ferroelectric liquid crystal having such excellent characteristic to a high-definition large-scale liquid crystal display device and a space modulation element for storing and processing light at a high speed.

However, the liquid crystal display device proposed by Clark and Lagerwall presents not few problems. Since the molecules of the ferroelectric smectic C phase liquid crystal have less symmetrical configuration and higher crystallization property than nematic liquid crystal molecules, it is difficult to uniformly orient the molecules in order to obtain a uniform display capability.

Figure 3:
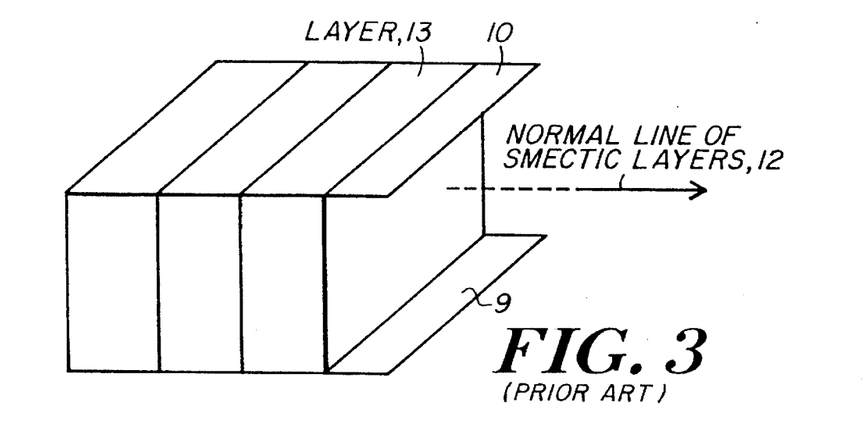
FIG. 3 is a schematic representation illustrating the bookshelf layer structure of a conventional ferroelectric liquid crystal cell.

In an initial model of the ferroelectric liquid crystal display device, the smectic C phase has a layer structure of so-called book-shelf type wherein the smectic layers are perpendicular to the substrates as shown in FIG. 3, which illustrates a liquid crystal cell including substrates 9 and 10, smectic layers 13, and the normal line 12 of the smectic layers.

Figure 4:
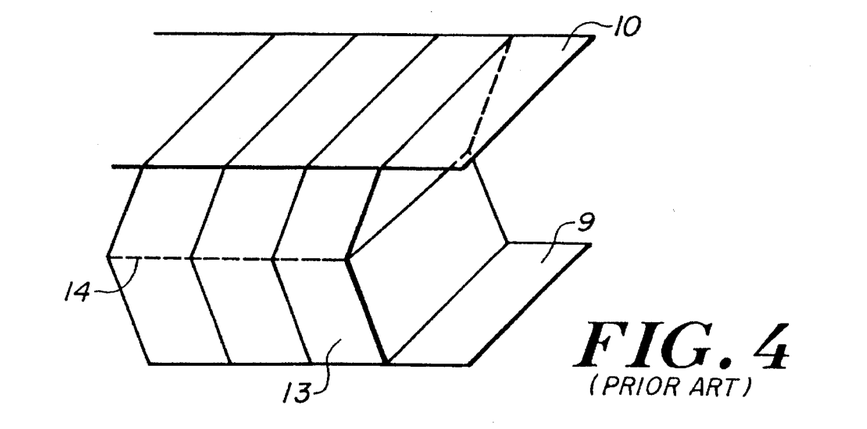
FIG. 4 is a schematic representation illustrating the chevron layer structure of a conventional ferroelectric liquid crystal cell.

A cell fabricated utilizing a conventional orientation treatment such as rubbing presents unexpected switching phenomena and optical characteristics, that is, its switching characteristics are completely different from the proposed model. It has been identified by small-angle X-ray scattering analysis that this is partly attributed to a bending layer structure called chevron as shown in FIG. 4, wherein reference numeral 14 denotes a juncture of the chevron structure called chevron interface. See T. P. Rieker, N. A. Clark et al, Phys. Rev. Lett., Vol. 59, p 2658 (1987). Another point different from the initial model is that, though the orientation of spontaneous polarization is uniform, liquid crystal molecules assume a uniform orientation as well as a twisted orientation between upper and lower substrates as reported by Y. Ouchi, H. Takezoe and A. Fukada in Japan Journal of Application Physics, Vol. 26, p 1 (1987). In particular, the rubbing orientation treatment, in many cases, results in the twisted orientation of ferroelectric liquid crystal due to a strong restricting force on a boundary surface. In general, the twisted orientation does not create effective optical difference of the orientation of molecular axes at the switching between two different states, and cannot provide high contrast characteristic, In order to realize the initial model proposed by Clark et al, some approaches have been proposed to eliminate such drawbacks. One of such approaches has been reported as attaining an oblique layer structure wherein the bending of the layers is prevented by providing a relatively large pretilt angle to the substrate prepared through SiO oblique evaporation technique. Another approach is to alter the layer structure into the book-shelf layer structure by applying a high-voltage alternating electric field to the cell of a bending structure, as proposed by Sato et at in the 12 th Liquid Crystal Symposium, Nagoya, 1F16 (1986). It has been reported that these two approaches obtained a high contrast characteristic.

However, the oblique evaporation of the first approach requires a difficult technique of forming uniform evaporation angle and a vacuum process, thereby presenting a critical production difficulty. In the second approach, it is also difficult to uniformly change the layer structure by the application of electric field, and the layer structure is, in most cases, gradually turned into the initial chevron structure over a long time. Therefore, this approach has not been put to a practical use yet.

To solve these problems, the present invention is to provide liquid crystal display element and device which present a high contrast characteristic despite the chevron structure thereof.

SUMMARY OF THE INVENTION

The present invention provides a liquid crystal display device comprising a pair of substrates, a transparent electrode formed on each of the substrates, an orientation film covering the transparent electrode and a liquid crystal sealedly sandwiched between the pair of substrates, wherein the orientation film comprises a polyimide which is formed by a condensation polymerization of 2,2-bis[4-(4-aminophenoxy) phenyl]propane as an amine component and 1,2,4,5-benzenetetracarboxylic dianhydride as an carboxilic acid component, and is subjected to a uniaxial orientation treatment, and the liquid crystal has a smectic layer structure with its bending direction which is aligned with the direction of the uniaxial orientation treatment.

DETAILED DESCRIPTION OF THE INVENTION

The orientation film according to the present invention is formed of a particular polyimide. The polyimide is obtained by the polymerization of 2,2-bis[4-(aminophenoxy)phenyl] propane as an amine component and 1,2,4,5-benzenetetracarboxylic dianhydride as a carboxilic acid.

For polymerization, two main components, the amine of 2,2-bis[4-(4-aminophenoxy)phenyl]propane and the carboxylic acid of 1,2,4,5benzenetetracarboxylic dianhydride can be mixed in a solvent under moderate warming to prepare a polyamic acid solution. The solution can be applied on a substrate which will form part of a liquid crystal cell, and then the substrate can be heated up to a predetermined temperature. As well as the aforethe main components, a small amount of 1-amino-4-trimethoxysilybenzene may be added as a subcomponent for polymerization. The molar ratio of the amine of 2,2-bis[4-(aminophenoxy)phenyl]propane to 1,2,4,5-benzenetetracarboxylic dianhydride is preferably 1:1 to 1:2. When 1-amino-4-trimethoxysilylbenzene is added in a small amount, preferable molar ratio of the raw materials are expressed by the following formulas:

$$0 < \frac{C}{A-B} \leq 2 \text{ and } 0.01 \leq \frac{C}{B+C}$$

Wherein A, B and C represent molar ratio of 1,2,4,5-benzenetetracarboxylic dianhydride, 2,2-bis[4-(4-aminophenoxy)phenyl]propane and 1-amino-4-trimethoxysilylbenzene, respectively. More preferable ratio are expressed by the following formulas:

$$1 \leq \frac{C}{A-B} \leq 2 \text{ and } 0.01 \leq \frac{C}{B+C}.$$

Examples of the solvents include Nmethylpyrrolidone (NMP), dimethylacetamide (DMAC), and diethylformamide (DMF).

The temperature for the moderate warming can be generally about 50 degrees centigrade or less. Preferably, the temperature for preparing the above polyamic acid solution is in the range of about 5 to 50 degrees centigrade. The concentration of the aforethe polyamic acid in the polyamic solution is adjusted for the viscosity suitable for application of the solution, typically about 0.1 to 30% by weight.

The substrate of the liquid crystal display device according to the present invention comprises a transparent insulation substrate such as a glass or plastic (e.g., polymethylmethacrylate plate, an electrode formed into a selected pattern thereon, and an insulation film formed further thereon.

The aforethe heating of the substrate is performed under such condition that the applied polyamic acid solution can be polymerized into polyimide, typically at a temperature of 130 to 300 degrees centigrade for 1 to 240 minutes. The aforementioned polyimide film is used as the orientation film after the uniaxial orientation treatment. The uniaxial orientation treatment is preferably a rubbing treatment.

Figure 12A:
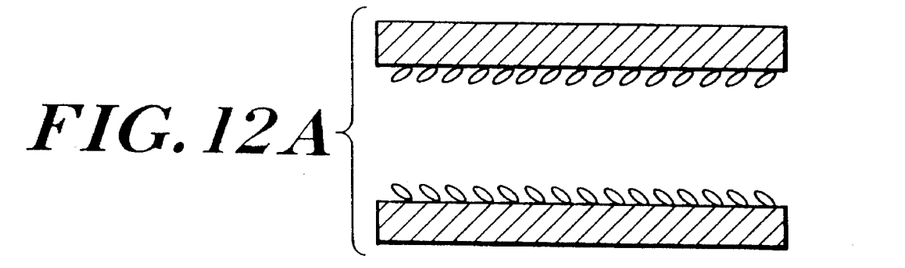
FIG. 12(a) to FIG. 12(c) are schematic representations illustrating three orientation arrangement for orienting ferroelectric liquid crystal molecules according to the present invention: (a) an orientation arrangement wherein the direction of a uniaxial orientation treatment on one substrate is the same as that on the other substrate; (b) an orientation arrangement wherein the direction of a uniform orientation treatment on one substrate is opposite to that on the other substrate; and (c) an orientation arrangement wherein a uniaxial orientation treatment is made on only one of the substrates.
Figure 12B:
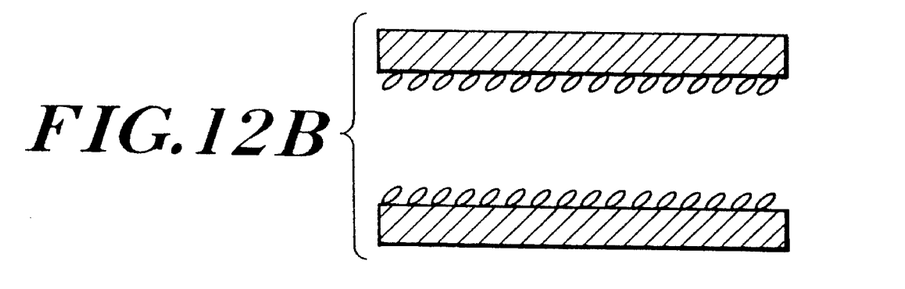
Figure 12C:
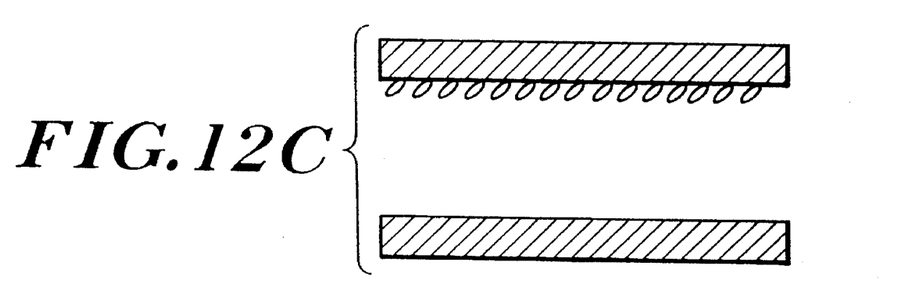

The liquid crystal display device of the present invention comprises a liquid crystal cell having substrates on at least one of which is formed the aforementioned orientation film, and the ferroelectric liquid crystal disposed therebetween. For example, As shown in FIG. 12, three orientation arrangements of a ferroelectric liquid crystal cell include: (a) an orientation arrangement wherein the direction of a uniaxial orientation treatment on one substrate is the same as that on the other substrate; (b) an orientation arrangement wherein the direction of a uniaxial orientation treatment on one substrate is opposite to that on the other substrate; and (c) an orientation arrangement wherein the uniaxial orientation treatment is made on only one of the substrates. It is known that an appropriate uniaxial orientation treatment allows liquid crystal molecules on the boundary between a substrate and liquid crystal to tilt from the substrate to cause so-called pretilt. It is also known that the pretilt direction can be controlled by the direction of the uniaxial orientation treatment and, for example, the pretilt direction is conformed with the rubbing direction. Among the aforementioned three orientation arrangements, the orientation arrangement (a) wherein the both substrates have the same direction of the uniaxial orientation treatment is preferable. In the orientation arrangement (b) wherein the directions of the uniaxial orientation treatment are opposite, many linear defects may occur, whereby the uniform orientation of the liquid crystal molecules may be hardly obtained. Finally, the orientation arrangement (c) is to be described wherein the orientation treatment is made on only one substrate. In general, a ferroelectric liquid crystal material has an INAC (Isotropic—Nematic—Smectic A—Smectic C) phase series, and in order to obtain a stable orientation in the smectic C phase, it is essential to obtain a stable orientation in the nematic phase. In the nematic phase, the ferroelectric liquid crystal has a helical structure, and a uniform orientation can be easily obtained between the substrates on both of which is made the uniaxial orientation treatment. If the orientation treatment is made on only one of the substrates, however, the ferroelectric liquid crystal tends to have a twisted orientation in the nematic phase. Therefore, when the liquid crystal is cooled into the smectic C phase, a stable orientation can be hardly obtained. Although such problem can be solved with a liquid crystal having no nematic phase, the liquid crystal tends to have a non-uniform orientation with small heterogeneous domains scattered in the smectic A phase.

Figure 5:
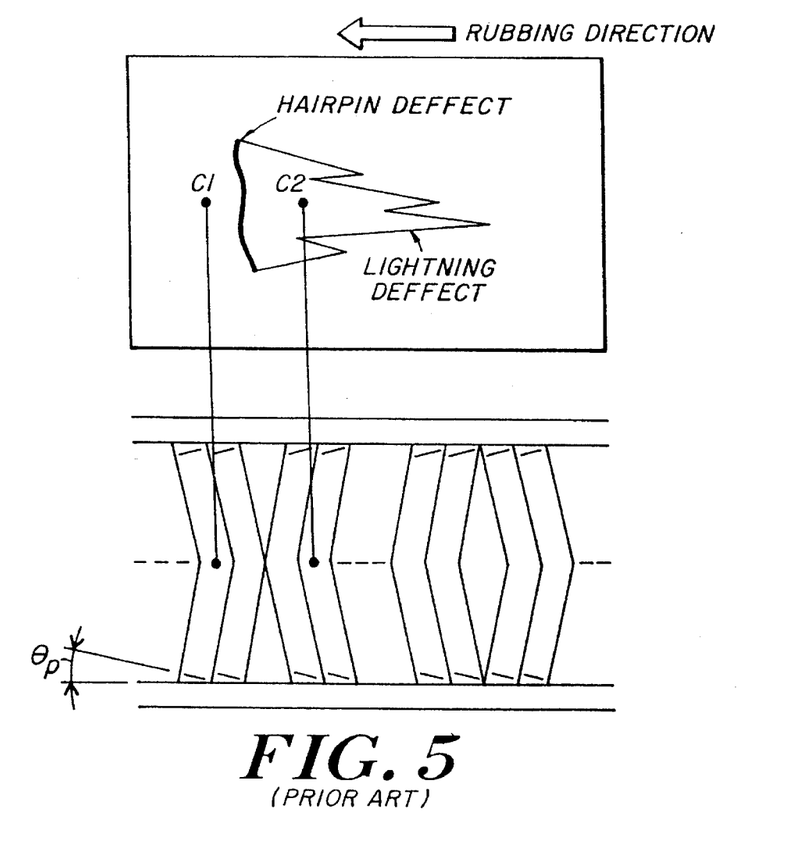
FIG. 5 is a schematic representation illustrating C1 and C2 orientations in a chevron layer structure of a conventional chiral smectic C phase.
Figure 6:
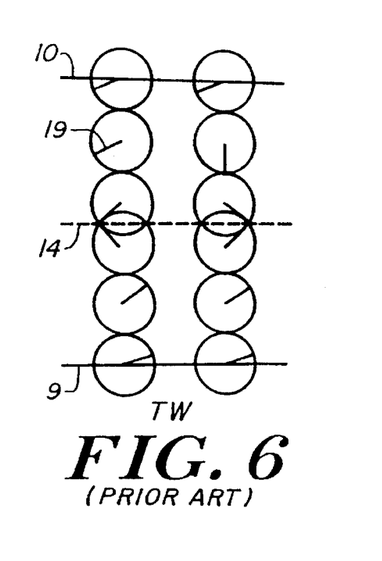
FIG. 6 is a schematic representation illustrating a twist orientation in a chevron layer structure of a conventional ferroelectric liquid crystal cell.
Figure 7:
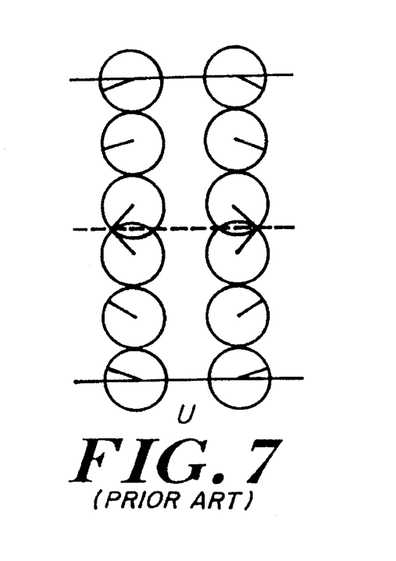
FIG. 7 is a schematic representation illustrating a uniform orientation in a chevron layer structure of a conventional ferroelectric liquid crystal cell.
Figure 8:
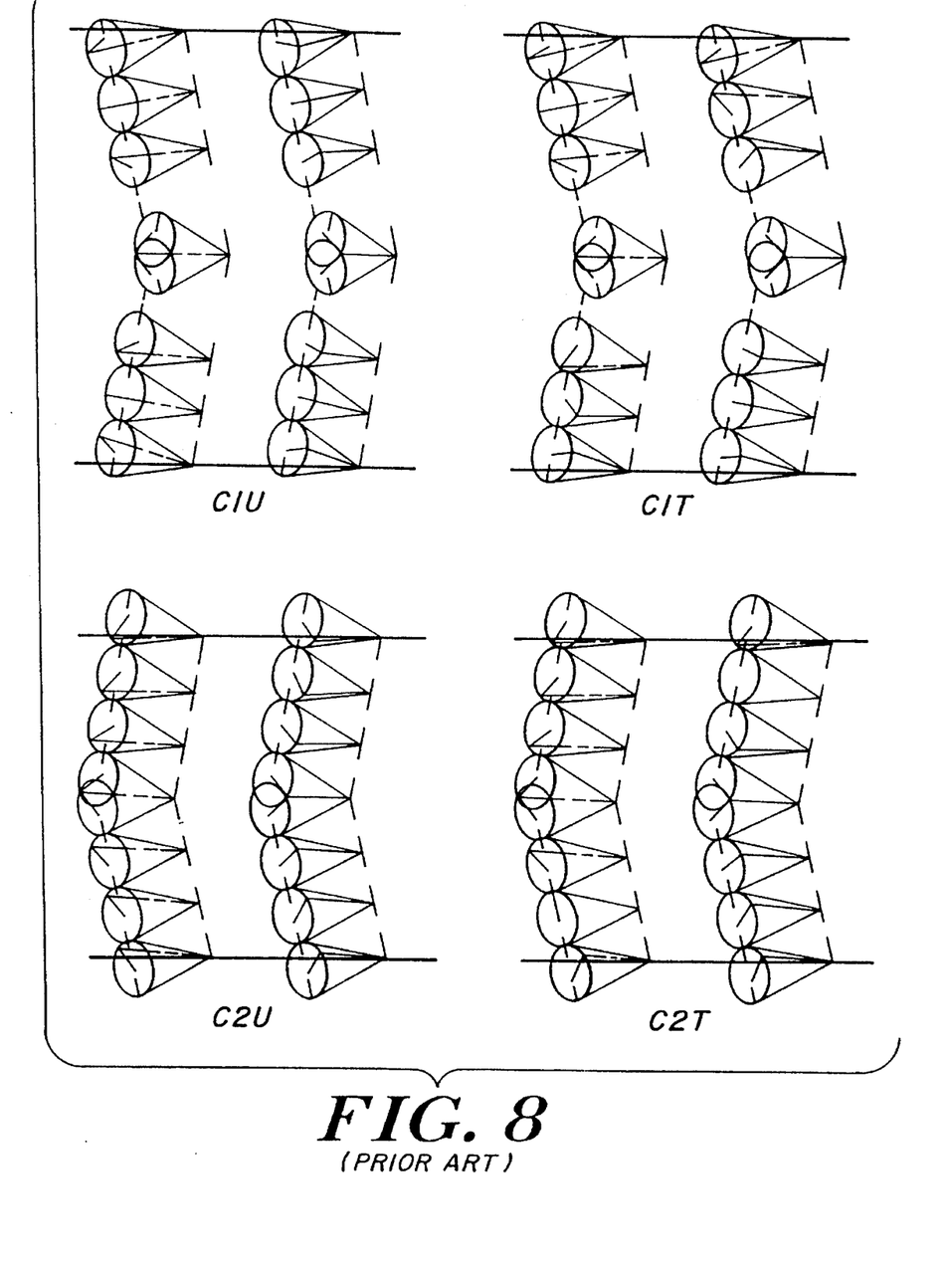
FIG. 8 is a schematic representation illustrating four orientation states C1U, C1T, C2U and C2T of a conventional ferroelectic liquid crystal cell.

On the other hand, a stable orientation can be relatively easily obtained if the ferroelectric liquid crystal having the INAC phase series is used in combination with a cell comprising a pair of substrates on both of which is made the uniaxial orientation treatment such as rubbing treatment in the same direction (parallel rubbing). However, there still exists some difficulty in obtaining a uniform orientation over the entire surface of the cell. This is attributed to two factors. One relates to the bending structure of the smectic layer. It is well known that the ferroelectric liquid crystal cell has the bending layer structure (chevron layer structure), wherein two regions exist as shown in FIG. 5(a) and FIG. 5(b). Kannabe et al referred to these two regions as C1 and C2 in view of their pretilt relation, as described in Ferroelectrics, Vol. 114, p 3 (1991). If there is no pretilting, these regions are related to the direction of the uniaxial orientation treatment such as rubbing. The other factor is twist (T) and uniform (U) orientations as respectively shown in FIGS. 6 and 7. The uniform orientation shows an extinction position, while the twist orientation shows no extinction position. In FIGS. 6 and 7, a reference numeral 19 denotes the C-director of a liquid crystal molecule. Koden et al reported in Japanese Journal of Application Physics, Vol. 30, p L1823 (1991) that three orientations C1U (C1 uniform), C1T (C1 twist) and C2 were obtained in a ferroelectric liquid crystal cell having high pretilt orientation films treated with parallel rubbing. Tagawa et al reported in Proc. of Japan Display '92 Hiroshima, p 519 (1992) that four orientations C1U, C1T, C2U (C2 uniform) and C2T (C2 twist) having different optical characteristics were obtained in a ferroelectric liquid crystal cell treated with parallel rubbing. FIG. 8 shows the molecular orientations in those states. C1T and C2T have no extinction position and therefore they are not suitable for a high contrast display. On the other hand, C1U and C2U have extinction positions and therefore have some possibility for high contrast display. As Koden et al reported, since C1U has a wider memory angle (an angle between the extinction position and the normal to the smectic layer which is observed when an electric field is not applied) than C2U, C1U may realize higher contrast display. However, Tagawa et al reported that C2U realized faster switching with shorter pulse width than C1U. C1U and C2U have different features with a possibility to realize a high contrast display, and there have been proposed various display modes, device structures and drive modes which utilize these features.

Drive modes for one such device utilizing a wide memory angle of C1U's feature was proposed by Koden et al in Proc. Japan Display '92 Hiroshima, p 579 (1992), which employed driving methods disclosed in Japanese Unexamined Patent Publication No. 1-59389 (1989) and disclosed in Sharp Giho, No. 50, p 45 (1991) by Numao.

Figure 9:
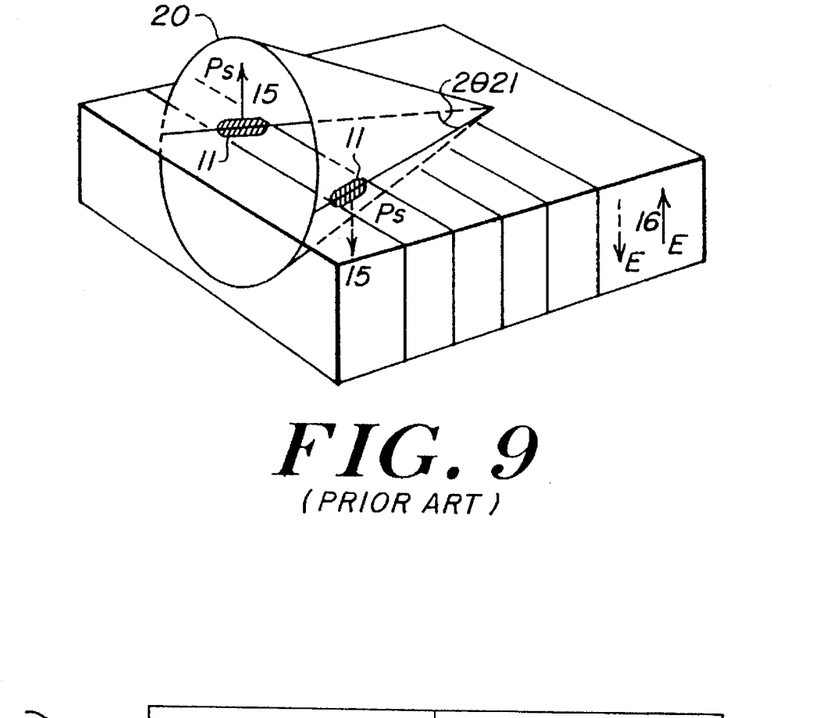
FIG. 9 is a schematic representation illustrating a condition of ferroelectric liquid crystal molecules in a smectic C phase of a conventional ferroelectric liquid crystal.

Another reported device drive mode utilizes the switching facility by electric pulses which is C2U's feature. In this drive mode, a ferroelectric liquid crystal (FLC) molecule 11 has a spontaneous polarization Ps15 in a direction perpendicular to its long axis, as shown in FIG. 9. The FLC molecule receives a force proportional to the vector product of an electric filed E16 and the spontaneous polarization Ps15, and moves on a conical locus 20 having an apex angle as twice wide as a tilt angle θ.

The FLC molecule 11 also receives another force which is proportional to the vector product of the square of the electric field E16 and dielectric anisotropy (difference between dielectric constants in the long axis and short axis directions of the molecule) Δε. Therefore, the force F exerted on the FLC molecule 1! is represented by the following equation:

$$F = K_1 \times Ps \times E + K_2 \times \Delta\epsilon \times E^2 \quad (1)$$

If a display panel contains an FLC material having a negative dielectric anisotropy Δε, the force generated by the spontaneous polarization Ps15 has a significantly larger effect on the force exerted to the FLC molecule than that generated by the dielectric anisotropy Δε<0 under an electric field lower than a certain level, while both of the forces have substantially the same effect under an electric field higher than a certain level.

Figure 10:
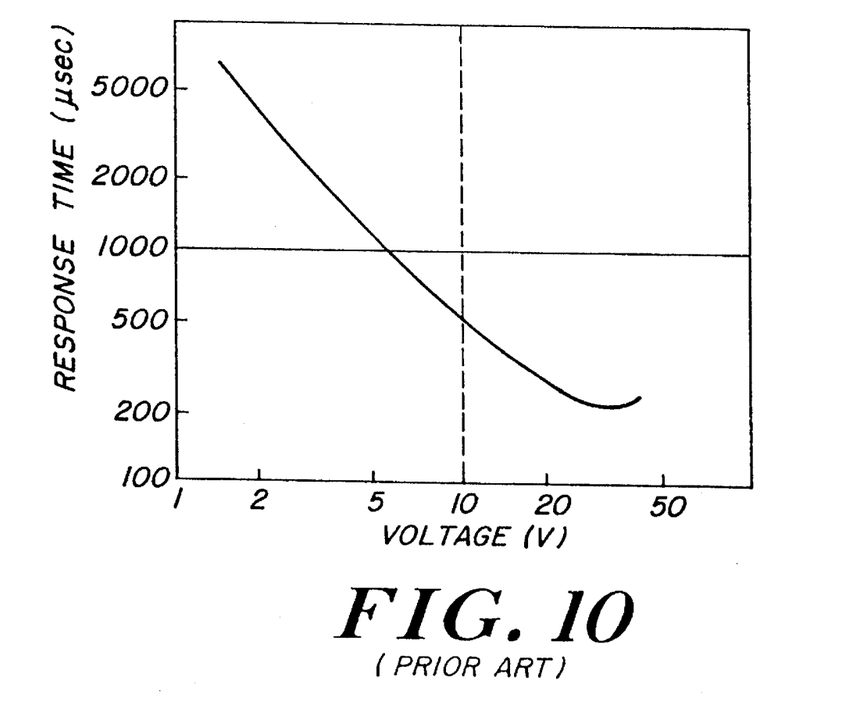
FIG. 10 is a graphic representation showing the characteristic of voltage vs. memory pulse width of an FLC material of $\Delta\epsilon<0$, which is cited from Japanese Unexamined Patent Publication No. 1-24234 (1989).

The effect of the negative dielectric anisotropy is known to show the minimum voltage in a voltage vs. response-speed characteristic, as shown in FIG. 10. Drive modes of FLC panels utilizing this phenomenon include, for example, arts disclosed in Japanese Unexamined Patent Publications No. 62-56933 (1987), No. 62-280824 (1987) and No. 124234 (1989), and the "Joers/Alvey" Ferroelectric Multiplexing Scheme disclosed in Ferroelectric Vol. 122, p 63 (1991). When these drive modes are used in combination with the FLC materials having a negative dielectric anisotropy, high contrast and therefore highly effective display devices can be obtained.

Figure 11:
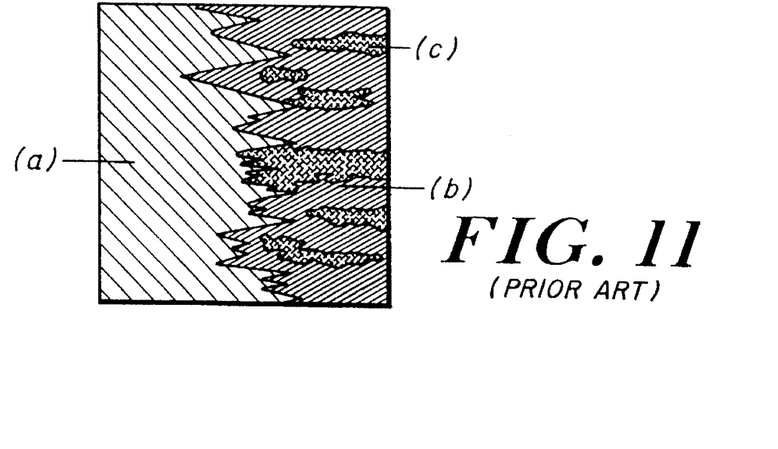
FIG. 11 is a schematic representation illustrating three orientation states of a conventional ferroelectric liquid crystal cell: (a) C2 uniform orientation; (b) C1 twist orientation; and (c) C1 uniform orientation.

However, though it has been reported that the "Joers/Alvey" Ferroelectric Multiplexing Scheme achieved a high contrast, an actual ferroelectric liquid crystal cell utilizing this scheme does not readily exhibit a high contrast, sometimes nor a stable switching. This is mainly attributed to the fact that the orientation of the ferroelectric liquid crystal cell affects the switching behavior and contrast. Take an example case wherein Merck's SCE-8 liquid crystal material having a negative dielectric anisotropy was injected into a ferroelectric liquid crystal cell with a thickness of 1.5 micrometers treated with parallel rubbing. FIG. 11 is a polarization-microscopic observation of the orientation states when the cell was driven according to the "Joers/Alvey" Ferroelectric Multiplexing Scheme. As shown in FIG. 11, there exist three different parts: (a) a part showing a high contrast; (b) a part showing a contrast ratio of less than 5; and (c) a part showing no switching.

The comparison of the aforethe four orientation states observed in the ferroelectric liquid crystal cell having a negative dielectric anisotropy shows that the cell does not present a high contrast because C1T and C2T have no extinction position and their dark states do not look black. The switching of C1U orientation is difficult, and even if the switching is successfully made, the C1U orientation is shifted into an orientation wherein C2 orientation is commingled therewith. On the contrary, it has been found by the present inventors that C2U orientation presents a high contrast.

If the dielectric anisotropy is not negative, the aforementioned drive mode proposed for a display device by Koden et al in Proc. Japan Display '92 Hiroshima, p 579 (1992) is effective. Though this drive mode requires C1U orientation, C2U orientation may be also effective for memory devices such as space modulation elements because C2U has an extinction position and distinct signal threshold. In this case, the distinct signal threshold means that the optical levels of stored optical conditions are clearly distinguished.

As mentioned above, the present invention primarily intends to realize a high contrast characteristic when a ferroelectric liquid crystal having a negative dielectric anisotropy is used for a display device. The present invention also allows a uniform orientation which has an extinction position and no defects regardless of the dielectric anisotropy, thereby providing a liquid crystal element characterized in that the bending direction of the smectic layer structure is the same as that of a uniaxial orientation treatment made on an orientation film.

With reference to the attached drawings, the present invention is hereinafter described by way of embodiments.

Figure 1:
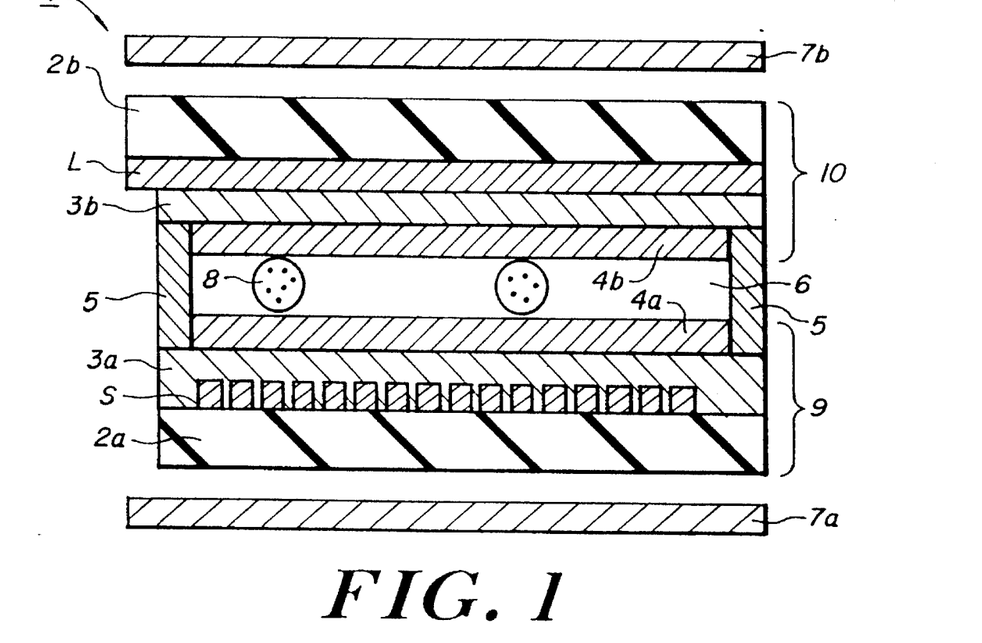
FIG. 1 is a cross-sectional view of a ferroelectric liquid crystal cell according to one embodiment of the present invention.

FIG. 1 is a schematic cross-sectional view of a ferroelectric liquid crystal display cell 1 according to one embodiment of the present invention. Two glass substrates 2a and 2b are disposed in an opposed relation. On the surface of one glass substrate 2a are disposed a plurality of transparent signal electrodes S parallel to each other which is made of indium tin oxide (ITO), and a transparent insulation film 3a of $SiO_2$ covering the electrode S. On the surface of the other glass substrate 2b opposing the signal electrode S are disposed a plurality of transparent scanning electrodes L parallel to each other in a direction perpendicular to the signal electrodes S, and a transparent insulation film 3b of $SiO_2$ covers the electrode L. On the surfaces of the insulation films 3a and 3b are respectively formed orientation films 4a and 4b of the present invention which are treated with a uniaxial orientation treatment such as rubbing. These two glass substrates 2a and 2b are bonded together with a sealant 5 with an injection opening remaining open via spacers 8 for controlling the thickness of a cell. A ferroelectric liquid crystal (FLC) 6 is injected into the space defined by the orientation films 4a and 4b from the injection opening which is thereafter sealed with the sealant 5. Two substrates 9 and 10 thus prepared are sandwiched between polarizer plates 7a and 7b which are arranged with their polarization axes being oriented perpendicular to each other.

EXAMPLE 1

As shown in FIG. 1, a plurality of transparent electrodes S having a thickness of 300 to 5000 angstroms, preferably 1000 to 3000 angstroms, were formed parallel to each other in a striped pattern on a glass substrate 2a. An $SiO_2$ electrode protection film 3a having a thickness of 300 to 5000 angstroms, preferably 500 to 2000 angstroms, was formed as covering the electrode S by way of sputtering. A carboxilic acid of 1,2,4,5-benzenetetracarboxylic dianhydride, an amine of 2,2-bis[4-(4-aminophenoxy)pheny)]propane and 1-amino-4-trimethoxysilylbenzene were mixed by molar ratio of 8:7:1.8 in Nmethylpyrrolidone (NMP) and polymerized at 15 degrees centigrade for five hours to obtain 10% polyamic acid NMP solution. This solution was applied on the electrode protection film 3a by way of spin coating. The substrate was preheated at 100 degrees centigrade for five minutes, and then heated at 200 degrees centigrade for one hour to obtain a polyimide film having a thickness of about 500 angstroms. In this case, the polyimide film was comprised of compounds of the typical formulae (1) and (2) and their precursor of the typical formula (3), and the imidization ratio was about 80 to 85%.

-continued (3)

Subsequently, a uniaxial orientation treatment was performed by rubbing the surface of the polyimide film with a rayon cloth to form a polyimide orientation film 4a, thus obtaining a complete substrate 9.

On the other hand, a plurality of transparent electrodes L were formed parallel to each other in a striped pattern on another glass substrate 2b in the same manner as above. A polyimide film was formed on an electrode protection film 3b on the glass substrate 2b in the same manner as the above. A uniaxial orientation treatment was performed by rubbing the surface of the polyimide film to form a polyimide orientation film 4b, thus obtaining a complete substrate 10.

Next, the substrates 9 and 10 were disposed so that the orientation films 4a and 4b were faced opposite to each other with their rubbing directions being substantially aligned with each other and with the transparent: electrodes S and L being orthogonal to each other. The substrates were spaced by 1.5 micrometers via spacers 8 and bonded together with an epoxy resin sealant 5 except for a liquid crystal injection opening.

A heated ferroelectric liquid crystal 6 (Merck's SCE-8) was injected between the substrates 9 and 10 by way of vacuum injection, and the injection opening was sealed with the sealant 5 to obtain a complete liquid crystal cell.

Polarizer plates 7a and 7b were disposed at the upper and lower locations of thus prepared cell such that their polarization axes were oriented essentially perpendicular to each other and one of the polarization axes of the polarizer plates was essentially aligned with either of the optical axes of the liquid crystal cell to obtain a complete liquid crystal display device 1.

Thus fabricated liquid crystal display device showed a uniform C2U orientation with no defects over the entire surface thereof. In addition, this liquid crystal display device realized a high contrast display when driven according to the "Joers/Alvey" Ferroelectric Multiplexing Scheme.

EXAMPLE 2

A ferroelectric liquid crystal display device was fabricated in accordance with the same procedure described in Example 1, except that the heating temperature for the orientation films was 300 degrees centigrade. In this case, the polyimide film was mainly comprised of the compound of the above formula (2), and the imidization ratio was 95% or higher.

Thus fabricated liquid crystal display device showed a uniform C2U orientation with no defects over the entire surface thereof. In addition, this liquid crystal display device realized a high contrast display when driven according to the "Joers/Alvey" Ferroelectric Multiplexing Scheme.

EXAMPLE 3

Ferroelectric liquid crystal display devices were fabricated in accordance with the same procedure described in Examples 1 and 2, except that the molar ratio of a carboxilic acid of 1,2,4,5-benzenetetracarboxylic dianhydride, an amine of 2,2-bis[4-(4-aminophenoxy)phenyl]propane and 1-amino-4-trimethoxysilylbenzene was changed to 5:4:1.8, 4:3:0.9, 60:59:1.8 and 1:1:0.

All of thus fabricated liquid crystal display devices showed a uniform C2U orientation with no defects over the entire surface thereof. In addition, these liquid crystal display devices realized a high contrast display when driven according to the "Joers/Alvey" Ferroelectric Multiplexing Scheme.

EXAMPLE 4

Ferroelectric liquid crystal display cells were fabricated in accordance with the same procedure described in Examples 1, 2 and 3, except that mixtures 1 to 6 having compositions shown in Table 1 were used as a ferroelectric liquid crystal material.

TABLE 1

| | Phase transition temperature (degrees centigrade) | | | | | Composition |
|---|---|---|---|---|---|---|
| | C | $S_C$ | $S_A$ | N | I | |
| SCE-8 | . −20 | . 59 | . 79 | . 100 | . | |
| Mixture 1 | . RT | . 57 | . 80 | . 100 | . | SCE-8:Compound1 = 4:1 |
| Mixture 2 | . RT | . 52 | . 77 | . 100 | . | SCE-8:ZLI3234B = 4:1 |
| mixture 3 | . RT | . 81 | . 95 | . 119 | . | SCE-8:Compound2 = 4:1 |
| Mixture 4 | . RT | . 65 | . 77 | . 99 | . | SCE-8:CompouNd3 = 9:1 |
| Mixture 5 | . RT | . 65 | . 88 | . 106 | . | SCE-B:Compound4 = 9:1 |
| Mixture 6 | . RT | . 59 | . 84 | . 105 | . | SCE-8:Compound5 = 9:1 |

Note: SCE-8 and ZLI3234B are available from Merck & Co., Ltd.

Compounds 1 to 5 which appear in Table 1 include the following compounds.

Compounds 1

All of thus fabricated liquid crystal display devices showed a uniform C2U orientation with no defects over the entire surface thereof. In addition, these liquid crystal display devices realized a high contrast display when driven according to the "Joers/Alvey" Ferroelectric Multiplexing Scheme.

EXAMPLE 5

Ferroelectric liquid crystal display cells were fabricated in accordance with the same procedure described in Examples 1 to 3, except that Chisso's CS-1014 was used as a ferroelectric liquid crystal.

Though thus fabricated liquid crystal display devices showed a uniform C2U orientation with no defects over the entire surface thereof, they could not be driven by the method shown in the "Joers/Alvey" Ferroelectric Multiplexing Scheme. This is because CS-1014 does not have a negative dielectric anisotropy. However, these liquid crystal display devices obtained distinct signal thresholds when they were operated as an optical memory device of a simple on-off type.

EXAMPLE 6

The liquid crystal cells fabricated in Examples 1 to 5 were heated up to an isotropic point, and then allowed to stand at a room temperature to be cooled to a ferroelectric point. All the liquid crystal display devices showed a stable C2U orientation and, except for CS-1014, realized a high contrast display when driven according to the "Joers/Alvey" Ferroelectric Multiplexing Scheme. The liquid crystal display device with CS-1014 obtained a distinct signal threshold when it was operated as an optical memory device of a simple on-off type.

EXAMPLE 7

As a reference example, ferroelectric liquid crystal display cells were fabricated in accordance with the same procedure described in Examples 1 to 6, except that polyvinyl alcohol (PVA) was used for orientation films.

These liquid crystal cells had the aforementioned four orientation states coexisting and a lot of defects. Though these liquid crystal devices employed the same liquid crystal materials as those fabricated in Examples 1 to 6, they functioned neither as a display device nor as an optical memory element. In particular, their performance was much lower than that observed in Examples 1 to 6 in terms of display contrast and uniformity.

As has been described, the present invention makes it possible to provide a high-contrast large-scale ferroelectric liquid crystal display device and an optical memory element having distinct optical levels. Furthermore, addition of a small amount of 1-amino-4-trimethoxysilylbenzene to the polyamide precursor solution improves its wettability (or fluidity) on the substrate, thereby facilitating the coating to form a uniform polyamide orientation film.

What is claimed is:

1. A liquid crystal display device comprising a pair of substrates, a transparent electrode formed on each of the substrates, an orientation film covering the transparent electrode and a liquid crystal sealedly sandwiched between the pair of substrates, wherein the orientation film comprises a polyimide which is formed by a condensation polymerization of 2,2-bis [4-(4-aminophenoxy)phenyl)propane as an amine component and 1,2,4,5-benzenetetracarboxylic dianhydride as an carboxylic acid component, and is subjected to a uniaxial orientation treatment, and wherein the liquid crystal has a smectic layer structure having a bending direction aligned with the direction of the uniaxial orientation treatment.

2. The liquid crystal display device of claim 1, wherein a direction of the uniaxial orientation of the orientation film covering the transparent electrode formed on each of the pair of substrates is the same.

3. The liquid crystal display device of claim 1, wherein the polyimide film is formed by the condensation polymerization in addition with a small amount of 1-amino-4-trimethoxysilylbenzene as a further amine component.

4. The liquid crystal display device of claim 3, wherein the amount of 1-amino-4-trimethoxysilylbenzene satisfies in a molar ratio defined by the formulas:

$$0 < \frac{C}{A-B} \leq 2 \text{ and } 0.01 \leq \frac{C}{B+C}$$

wherein A, B and C represent molar ratio of 1,2,4,5-benzenetetracarboxylic dianhydride, 2,2-bis(4-(4-aminophenoxy)phenyl]propane and 1-amino-4-trimethoxysilyl benzene, respectively.

* * * * *